Figure 1:
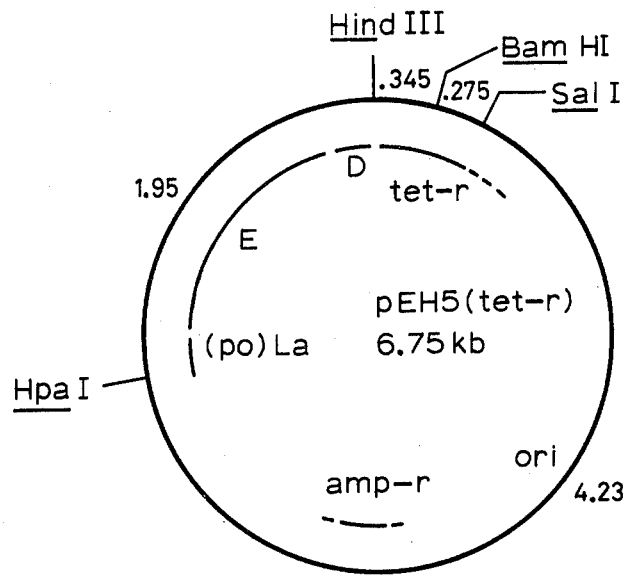

United States Patent [19]

Carey et al.

[11] 4,349,629

[45] Sep. 14, 1982

[54] PLASMID VECTORS, PRODUCTION AND USE THEREOF

[75] Inventors: Norman H. Carey, Chinnor; John S. Emtage, Amersham Hill; William C. A. Tacon, High Wycombe, all of England; Robert A. Hallewell, San Francisco, Calif.

[73] Assignee: G.D. Searle & Co., Skokie, Ill.

[21] Appl. No.: 154,489

[22] Filed: May 29, 1980

[30] Foreign Application Priority Data

Jun. 1, 1979 [GB] United Kingdom ............... 7919245

[51] Int. Cl.$^3$ ............................................. C12N 15/00
[52] U.S. Cl. ..................................... 435/172; 435/68; 435/317
[58] Field of Search ................... 435/68, 70, 91, 172, 435/317

[56] References Cited

U.S. PATENT DOCUMENTS 4,237,224 12/1980 Cohen et al. ................... 435/849 X

OTHER PUBLICATIONS

Itakura et al., *Science*, 198, 1056-1063, (1977).
Bolivar et al., *Gene*, 2, 95-113, (1977).
Hershfield et al., *J. Bacteriol.*, 126(1), 447-453, (1976).
Bennett et al., *Proc. Natl. Acad. Sci. USA*, 73(7), 2351-2355, (1976).
Collins et al., *Proc. Natl. Acad. Sci. USA*, 73(11), 3838-3842, (1976).
Warren et al., *Nature*, 274, 259-261, (1978).
Goeddel et al., *Proc. Natl. Acad. Sci. USA*, 76(1), 106-110, (1979).

*Primary Examiner*—Esther M. Kepplinger
*Attorney, Agent, or Firm*—Albert Tockman; Albin James Nelson

[57] ABSTRACT

A plasmid having an insertion site for a eukaryotic DNA fragment adjacent to a bacterial promoter and downstream from a prokaryotic ribosome binding site and initiator codon such that the bacterial promoter controls transcription and translation of an inserted DNA fragment is disclosed.

The production and use of such plasmids is also disclosed.

In general terms, one aspect of the present invention relates to a series of plasmid vectors having the basic characteristic of a Hind III insertion site adjacent to a tryptophan promoter and also a gene for tetracycline resistance. The plasmid vectors are by virtue of the structure thereof ideally suited to receive at the Hind III site an inserted eukaryotic DNA fragment the transcription and translation of which is under the control of the tryptophan promotor.

14 Claims, 17 Drawing Figures

PLASMID VECTORS, PRODUCTION AND USE THEREOF

This invention relates to plasmid vectors, to the production thereof and to the use thereof; more particularly, it relates to plasmid vectors adapted to receive and transcribe inserted DNA fragments.

The genetic content of most organisms is in the form of DNA. This genetic information is expressed by a complex series of reactions involving transcription of the DNA into RNA and the subsequent translation of the RNA into protein.

In bacterial cells, transcription and translation are closely linked. The amount of a given protein is controlled by the amount of transcription occurring. The tryptophan operon and the control thereof is a good example on this point. Bacteria synthesise tryptophan by a series of biochemical reactions involving five enzymes. The genetic information for producing these enzymes is so organized that the individual genes follow consecutively in the genome and are all controlled from a single site, the operator. Control of transcription operates on a feed-back principle, i.e. in the presence of tryptophan, the operon is blocked or repressed, while, in the absence of tryptophan, it is de-repressed. In the de-repressed state, transcription is initiated at the promoter (a region of DNA near the operator having a high affinity for RNA polymerase) and proceeds through the operator into the structural genes of the operon.

It is known that eukaryotic DNA fragments may be inserted into bacterial plasmids, (see, for example, Roychoudhury, R., et al, (1976), Nucleic Acids Research, 3, 863–877; and Scheller, R. H., et al, (1977), Science, 196, 177–180). However, it is evident that introduced eukaryotic promoter sequences are poorly recognised by bacterial cells, for example by E. coli RNA polymerase in vivo. Thus, although it has been reported that it has been possible to complement bacterial mutations by DNA fragments from yeast, the extent of expression of the cloned gene was low and produced slow growing bacteria, (see, for example, Carbon, J., et al, (1977), Recombinant Molecules: Impact on Science and Society, Raven Press, New York, 355–378).

Similarly, cloned mouse mitochondrial DNA transcription in E. coli occurred from the wrong strand, (see, for example, Brown, W. M., et al, (1976), Cell, 7, 517–530).

The structure of the plasmid vectors according to the present invention is based upon the provision of an insertion site, particularly a Hind III site, for a chosen eukaryotic DNA fragment, which insertion site is adjacent to a bacterial promoter, e.g. a trp promoter, so that the transcription and translation of the DNA fragment are controlled by the promoter. The present plasmids are generally also provided in the region immediately following the insertion site, with the gene for tetracycline resistance, so that, after insertion of the chosen DNA at the insertion site, transcription and translation of the inserted DNA controlled by the promoter may conveniently be confirmed, since, when it has occurred, tetracycline resistance is preserved, and, in most cases, when it has not, tetracycline resistance is destroyed.

One embodiment of the present invention relates to a plasmid having an insertion site for a eukaryotic DNA fragment adjacent to a bacterial promoter and downstream from a prokaryotic ribosome binding site and initiator codon such that the bacterial promoter controls transcription and translation of an inserted DNA fragment.

Such a plasmid may be prepared by a process which comprises cloning a bacterial promoter into an isolated plasmid, determining the position of an intended insertion site and providing the insertion site, if it is not already present.

Such a plasmid vector may be produced using such a plasmid by digesting cellular DNA with a specific restriction enzyme, isolating a promoter-containing fragment and cloning the fragment into a suitable bacterial plasmid.

In another embodiment, the present invention relates to such a plasmid having inserted therein at the insertion site a eukaryotic DNA fragment.

The eukaryotic DNA fragment may be inserted into the prepared plasmid by known techniques.

For purposes of exemplification, one of the present plasmids is that having the characteristics represented diagrammatically in FIG. 1 of the accompanying drawings, viz. a molecular length of 6750 bp, a Hind III site, a Bam HI site at 346 bp from the Hind III site, a Sal I site at 275 bp from the Bam HI site, a Hpa I site at 4230 bp from the Sal I site and 1950 bp from the Hind III site, the plasmid having the trp promoter, the E gene and part of the D gene in the portion of 1950 bp extending between the Hpa I site and the Hind III site and the gene for ampicillin resistance in the portion of 4800 bp between the Hind III site and the Hpa I site.

Again for purposes of exemplification, this plasmid, referred to herein as pEH5, may be produced as follows:

(a) Isolation of the Hind III trpE fragment

This fragment may be obtained either by Hind III (EC3.1.23.21) digestion of DNA from most strains of E. coli., e.g. E. coli strain W3110, or by Hind III digestion of the plasmid, pRH1/trpE. pRH1 was itself obtained by Eco RI (EC3.1.4.32) digestion of E. coli plasmids pDS1118 and pML2, ligation of the thus-obtained fragments and selection for ampicillin and kanamycin resistance. Hind III digestion of pRHI and ligation with Hind III digested DNA from strain E. coli W3110, followed by transformation into strain W3100 trp o$\tilde{E}$V1 and culture in the absence of tryptophan, produced pRH1/trpE.

(b) Cloning the Hind III trpE fragment

Figure 2:
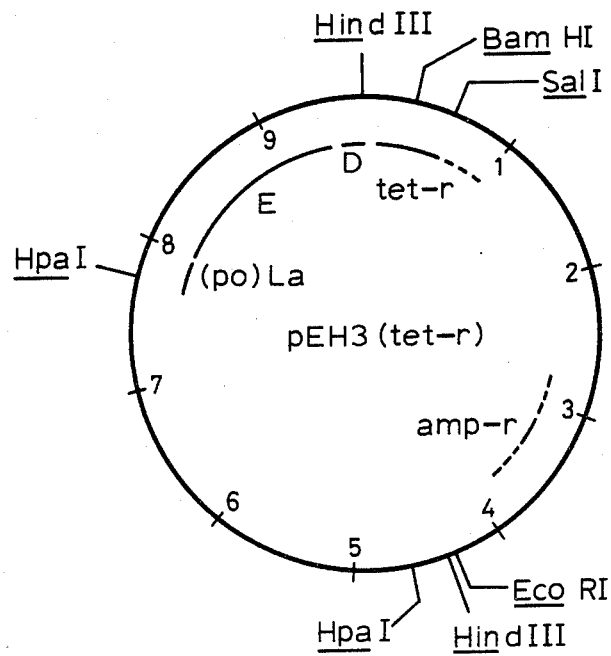
Figure 3:
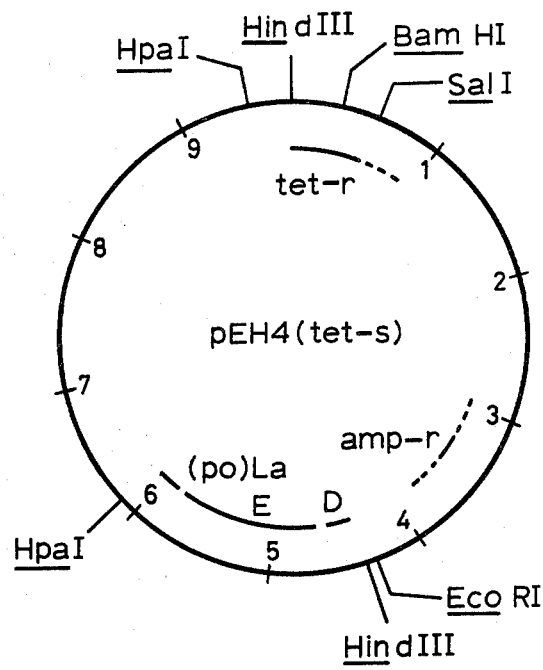

The Hind III trpE fragment, obtained as described above, was covalently ligated to a fragment obtained by Hind III restriction of the plasmid pBR322, (see, for example, Bolivar, F., et al, (1977), Gene, 2, 95–113). The ligated DNA was used to transform E. coli W3110 trp o$\tilde{E}$V1 and colonies selected for ampicillin resistance and tryptophan complementation. The plasmids obtained were found to be of two types, depending on the orientation of the fragments during ligation; these two plasmids, referred to herein as pEH3 and pEH4, are illustrated in FIGS. 2 and 3, respectively, of the accompanying drawings. The plasmid pEH3 was selected on the basis of its tetracycline resistance and used for the next stage of the production of the present plasmids. The plasmid pEH3 has the following characteristics:

A molecular length of 9866 bp; a Hind III site; a Bam I site 346 bp from the Hind III; a Sal I site 275 bp from the Bam I; and Eco RI site 3709 bp from the Sal I; a second Hind III site 31 bp from the Eco RI; a Hpa I site 305 bp from the second Hind III; a second Hpa I site 3250 bp from the first Hpa I and 1950 bp from the first Hind III, the plasmid having the trp promoter, the E gene and part of the D gene in the portion of 1950 bp between the second Hpa I and the first Hind III sites; the gene for tetracycline resistance immediately following the first Hind III site and the gene for ampicillin resistance in the portion 3709 bp between the Sal I and the Eco RI sites.

(c) Deletion of the Hind III site proximal to the Eco RI site in pEH3 pEH3 was digested with Eco RI to produce linear molecules which were digested with exonuclease III (EC 3.1.4.27) and then with S1 nuclease (EC 3.1.4-) to remove the 5'-protruding tails and to produce blunt ends. Then, the linear molecules were ligated with T4-induced DNA ligase (EC 6.5.1.1) and the thus-obtained plasmid was used to transform the trp oEV1 strain and selected for trp complementation and ampicillin resistance to obtain the plasmid according to the present invention, referred to as pEH5, (illustrated in FIG. 1).

The plasmid pEH4 has the following characteristics:

A molecular length of 9866 bp; a Bam I site 346 bp from the Hind III; a Sal I site 275 bp from the Bam I; an Eco RI site 3709 bp from the Sal I; a second Hind III site 31 bp from the Eco RI; a Hpa I site 1950 bp from the second Hind III site; a second Hpa I site 3250 bp from the first Hpa I and 305 bp from the first Hind III, the plasmid having the trp promoter, the E gene and part of the D gene in the portion of 1950 bp between the second Hind III and the first Hpa I sites; the gene for tetracycline resistance immediately following the first Hind III site and the gene for ampicillin resistance in the portion of 3709 bp between the Sal I and the Eco RI sites, the plasmid being referred to as pEH4. pEH4 may be produced in a similar manner to pEH3, except that selection is effected on the basis of the tetracycline sensitivity thereof.

As mentioned above, a particular utility of the present plasmids is that they have a clearly defined site convenient for the introduction of a desired eukaryotic DNA fragment and that the structure of the plasmids is such that the transcription of the introduced DNA is controlled by the promoter, particularly, a trp promoter, associated with the defined introduction site, for example, the Hind III site of the plasmid pEH5 (illustrated in accompanying FIG. 1). This plasmid therefore represents a valuable final intermediate from which may be produced plasmids having inserted at the insertion site, for example the Hind III site, genetic information in the form of suitably modified DNA designed to produce a desired polypeptide product.

In general terms, the preparation of the required DNA, the modification thereof for insertion and the insertion procedures, as well as the subsequent processes for protein production, are known and may be summarised and exemplified as follows:

(1) Source of the DNA to be inserted

DNA for insertion may be obtained by a variety of procedures. For example, oligonucleotides of various lengths may be synthesized by known procedures, (see, for example, Hsiung, et al, (1979), Nucleic Acids Research, 6, 1371-1385).

Several oligonucleotides may be assembled, in consequence of the specific base pairing properties thereof, into longer, double-stranded molecules. The component oligonucleotides of this molecule may be joined (ligated) by the enzyme DNA ligase.

Alternatively, DNA molecules of desired genetic specificity may be synthesized by the use of the enzyme reverse transcriptase, using RNA of the desired specificity as template. The RNA may be isolated from cells by known procedures.

(2) Preparation of the DNA for insertion

DNA may be modified for insertion into the plasmid by a variety of procedures. For example, DNA prepared as described above may be extended at the 3' terminus of each of the double strands by means of the enzyme terminal transferase (EC 2.7.7.31) to give a homopolymeric single-stranded extension. The 3' terminus of the Hind III digested plasmid may be similarly extended. If the extension of the prepared DNA is $(dA)_n$ and of the plasmid $(dT)_n$ or vice versa, or if the extension of the prepared DNA is $(dG)_n$ and of the plasmid $(dC)_n$ or vice versa, then the DNA for insertion and the plasmid may be hybridized by these single-stranded extensions such that circular molecules are formed where the prepared DNA is inserted at the Hind III site of the plasmid. Such plasmids may be used to transform E. coli cells and colonies of the transformants selected by known procedures, (see, for example, Glover, D., New Techniques in Biophysics and Cell Biology, (Eds. Pain, R. H., and Smith, B. J.), 8, 125-145, (Wiley, New York, 1976). Alternatively, the ends of the DNA prepared as described above may be ligated with the enzyme DNA ligase to short double-stranded DNA molecules, (Hind III linkers, obtainable from Collaborative Research, Waltham, Mass., U.S.A.), which contain the sequence recognised by the restriction enzyme Hind III. Digestion of these molecules with this enzyme following the ligation, will generate Hind III termini at the ends of the prepared DNA. The prepared DNA may then be inserted into the plasmid following digestion with Hind III by known procedures.

(3) Preparation of peptide

The known mechanisms of operation of bacterial promoters together with the data above, lead to the conclusion that when the operator is open, transcription from the promoter will proceed from trpE and trpD through the Hind III site and into regions of the genome beyond the Hind III site. Translation of the transcription product will give a read-through polypeptide linked to the D gene (unless a termination codon is incorporated into the insert). The polypeptide produced may be identified by known methods, for example by transferring the plasmid to a strain which produces minicells, (see, for example, Meagher, R. B., (1977), Cell, 10, 521-536), in which the polypeptide products of plasmid genomes are easily distinguished, or by immunological procedures, (see, for example, Broome, S., and Gilbert, W., (1978), Proc. Natl. Acad. Sci. U.S.A., 75, 2746-2749)

The read-through polypeptide may be purified by known procedures and the desired polypeptide product generated by digestion of the polypeptide by specific chemical or enzymic means.

The plasmid pEH5 according to the present invention may also be used as a source of DNA from which may be constructed a further series of plasmid vectors, the socalled "pWT" series.

The plasmid pEH5 may be treated with the restriction endonuclease Hinf I (EC 3.1.23.22) to obtain therefrom a fragment of approximately 497 bp containing the complete tryptophan promoter, leader sequence and the first seven amino acids of the trpE. The thus-obtained Hinf I fragment may then be cloned into the Hind III site of the known plasmid pBR322. This cloning may be effected by treating the Hinf I ends of the fragment with DNA polymerase I (EC.2.7.7.7) and subjecting the DNA filled Hinf I fragments to the action of Hind III linkers in the presence of DNA ligase and Hind III restriction endonuclease sequentially to provide the fragment with Hind III "sticky ends."

Thereafter, the Hinf I fragment may be cloned into the plasmid pBR322 by Hind III restriction of the pBR322 and ligation of the restricted plasmid with the Hinf I fragment.

The Hinf I fragment will be inserted into the Hind III site of pBR322 in one of two orientations as described above in connection with pEH3 and 4. One of these in which the trp promoter is transcribed in the direction of the tet genes is selected by restriction enzyme analysis of individual clones. (The sequence of pBR322 is known, see for example, Sutcliffe, J. G., Cold Spring Harbor Symposium on Quantitative Biology, (1978), XL11, 77–90. The sequence of the trp promoter/operator is also known, see, for example, Bennett, G. N., et al. (1978), J. Mol. Biol., 121, 113–137, and Lee, F., et al. J. Mol. Biol., (1978), 121, 193–217.)

Figure 4:
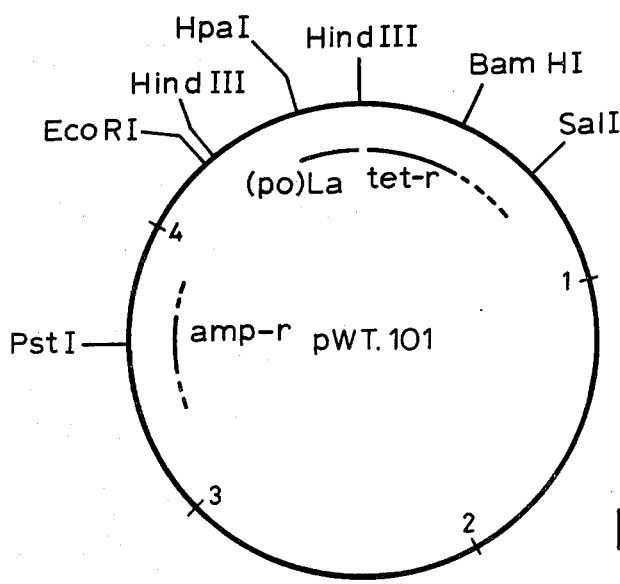

The resulting plasmid is referred to herein as pWT101, the structure of which is illustrated in FIG. 4 of the accompanying drawings. This plasmid has the following characteristics:

A molecular length of 4874 bp; an Eco RI site; a Hind III site 31 bp from the Eco RI; a Hpa site 313 bp from the Hind III; a second Hind III site 199 bp from the Hpa I; a Bam I site 346 bp from the second Hind III; a Sal I site 275 bp from the Bam I; a Pst I site 2958 bp from the Sal I and 752 bp from the Eco RI; the gene for tetracycline resistance extending from the region of the Hpa I site to beyond the Sal I site; the gene for ampicillin resistance in the region of the Pst I site and the cloned portion of the trp operon comprising the region between the promoter and the first portion of the E gene between the Hpa I and the second Hind III site.

By virtue of the above-illustrated production thereof, the plasmid pWT101 has two Hind III sites, one at each end of the inserted Hinf I fragment from the original pEH5.

In order to ensure that inserted DNA will be positioned adjacent to the tryptophan promoter, it is necessary to delete the Hind III site upstream of the tryptophan promoter and this may be achieved by restriction of the plasmid pWT101 with the restriction endonuclease Eco RI, digestion with exonuclease III and S1, treatment with DNA polymerase I (to fill any asymmetrical ends produced by S1 nuclease digestion) and ligation of the free ends of the plasmid to produce a derivative of pWT101, referred to herein as pWT111, which has only one Hind III site and that downstream of the trp promoter.

Accordingly, the present invention also relates to a plasmid pWT111, adapted to receive inserted DNA at the Hind III site, resulting in the DNA being under the direct influence of the trp promoter. Transcription and translation of the inserted DNA may easily be confirmed since the plasmid contains downstream of the inserted fragment the gene for tetracycline resistance so that transcription through the inserted DNA proceeds on through the tet-r gene producing tetracycline resistance which is not produced if transcription through the inserted DNA does not take place.

Depending on the nature of the DNA fragment it is desired to insert, it is necessary to ensure correct phasing in the plasmid matched to that of the DNA to be inserted. Thus, double-standard cDNA prepared by reverse transcription from mRNA, if complete, normally contains a length of nucleotides as a leader region prior to the protein sequence. Because of this, translation of the protein as part of a fused polypeptide in a plasmid, such as pWT111, (cloned in at the Hind III site), becomes dependent on the number of nucleotides in the leader, i.e. incomplete reverse transcription may reduce the leader sequence, so altering the reading frame. For this reason, the construction of expression plasmids able to translate for all three reading frames is essential.

Plasmid pWT111 allows translation of DNA inserted at the Hind III site as a fused polypeptide in one reading frame only (if the inserted DNA has its own functional ribosome binding site, then this does not apply.) Translation starts with the first 7 amino acids of trpE, followed by 2 amino acids from the Hind III linker DNA and would then proceed into the inserted sequence. If no stop codons were present in this sequence, then translation would terminate at the first stop codon in the tetracycline region.

The nucleotide sequence across the Hind III site of pBR322 shows that, for pWT111, the first stop codon is 26 nucleotides downstream from the Hind III site.

To change the phasing from the Hind III site of pWT111, the plasmid may be restricted with Hind III, the 5' extensions filled with DNA polymerase I and Hind III linker DNA ligated. Restriction with Hind III, to remove excess linker and produce "sticky ends," and religation produced "pWT121". This procedure adds 14 bp of DNA and alters the reading frame from the new Hind III site (the old site is now incomplete) by plus one nucleotide.

The third reading frame, i.e. pWT111 plus 2 nucleotides, was obtained by repeating the same series of reactions on pWT121 and the resulting plasmid is referred to as "pWT131".

Figure 5:
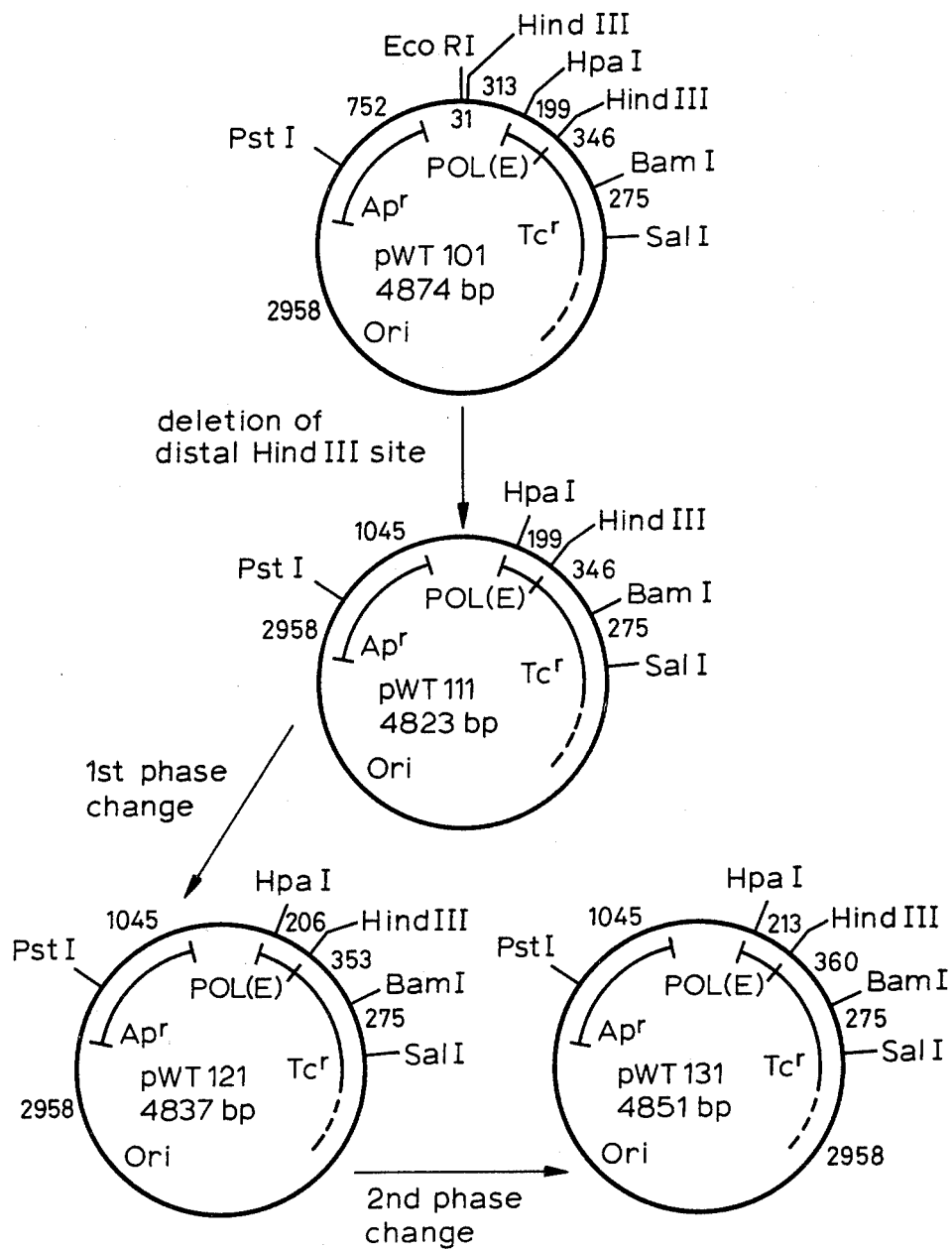

The structure of the plasmids pWT111, pWT121 and pWT131 is shown in FIG. 5 of the accompanying drawings. The structure may be further defined as follows:

pWT111

A molecular length of 4823 bp; a Hpa I site; a Hind III site 199 bp from the Hpa I; a Bam I site 346 bp from the Hind III; a Sal I site 275 bp from the Bam I; a Pst I site 2958 bp from the Sal I and 1045 bp from the Hpa I; the gene for tetracycline resistance extending from the region of the Hpa I site to beyond the Sal I site; the gene for ampicillin resistance in the region of the Pst I site and the cloned portion of the trp operon comprising the region between the promoter and the first portion of the E gene between the Hpa I and the Hind III sites.

pWT121

A molecular length of 4837 bp; a Hpa I site; a Hind III site 206 bp from the Hpa I; a Bam I site 353 bp from the Hind III; otherwise as pWT111.

pWT131

A molecular length of 4851 bp; a Hpa I site; a Hind III site 213 bp from the Hpa I; a Bam I site 360 bp from the Hind III; otherwise as pWT111.

The sequences around the Hind III site of pWT111, 121 and 131 are as follows:

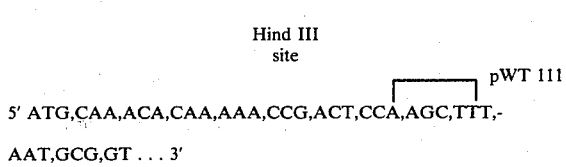

5' ATG,CAA,ACA,CAA,AAA,CCG,ACT,CCA,AGC,TTT,-AAT,GCG,GT ... 3'

-continued

5' ATG,CAA,ACA,CAA,AAA,CCG,ACT,CCA,AGC,-     pWT 121

Hind III
site
⌐¯¯¯¯¯¯¬
TCC,AAG,CTT,GGA,GCT,TTA,ATG,C . . . 3'

5' . . . AAA,CCG,ACT,CCA,AGC,TCC,AAG,CTG,-     pWT 131

Hind III
site
⌐¯¯¯¯¯¬
CAA,GCT,TGG,AGC,TTG,GAG,CTT,TAA,TG . . . 3'

(For convenience, the above sequences show only one strand of the DNA).

As an illustration, the effectiveness of the plasmids pWT111, 121 and 131 as vectors for inserted DNA may be seen from the results obtained by insertion into pWT121, the plasmid of correct phase in this case, of a synthetic fowl plague virus (FPV) gene, (see, for example, G. B. Patent Application No. 80 10777; and Emtage, J. S., et al, (1980), Nature, 283, 171–174).

The above-mentioned synthetic FPV gene may be cloned into pWT 121 as follows:

The plasmid pWT121 was restricted with Hind III and treated with alkaline phosphotase (EC 3.1.3.1) to remove the 5'-phosphate groups. Hind III linkers were ligated to the ends of the synthetic FPV gene, which was then treated with Hind III restriction endonuclease to produce Hind III sticky ends. The thus-treated synthetic FPV gene and the Hind III restricted pWT121 were then ligated to obtain the plasmid pWT121/FPV. Alternatively, the synthetic FPV gene may be cloned in plasmid pBR322 and then transferred to pWT121 in known manner.

Figure 6:
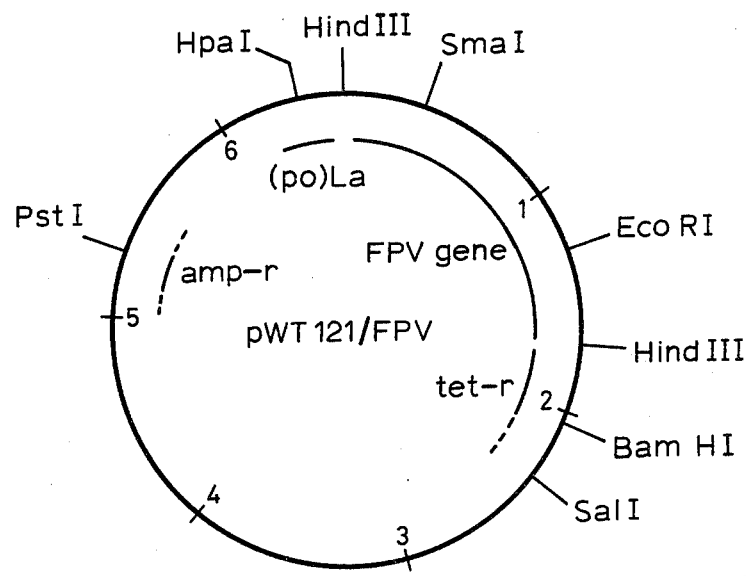

The general structure of the plasmid pWT121/FPV is illustrated in FIG. 6 of the accompanying drawings. The structure may be further defined as follows:

A molecular length of 6532 bp; a Hind III site; a Sma I site 365 bp from the Hind III; an Eco RI site 910 bp from the Sma I; a second Hind III site 460 bp from the Eco RI; a Bam HI site 353 bp from the second Hind III; a Sal I site 275 bp from the Bam HI; a Pst I site 2958 bp from the Sal I; a Hpa I site 1045 bp from the Pst I and 206 bp from the first Hind III; the synthetic FPV gene in the portion of 1735 bp between the first and the second Hind III sites; the gene for tetracycline resistance extending from the second Hind III site to beyond the Bam HI site and the gene for ampicillin resistance in the region of the Pst I site.

Depending on the orientation of the FPV gene, the plasmid was found to be tetracycline resistant (as illustrated in FIG. 6) or tetracycline sensitive with the FPV gene in the reverse orientation.

Transformed E. coli colonies containing the pWT121/FPV plasmids with the haemagglutinin(HA) gene in either orientation were screened for FPV-HA antigen. It was found that tetracycline resistant colonies expressed FPV-HA antigen, confirming correct insertion of the synthetic FPV gene. Those colonies with the FPV gene oriented as illustrated in FIG. 6 showed tetracycline resistance and those with reverse orientation were tetracycline sensitive. In the former case, the expression of the HA antigen was under trp control.

FPV-HA antigen expression may be confirmed as follows:

E. coli colonies containing the tetracycline resistant pWT121/FPV plasmid described above were screened for FPV-HA antigen using a solid-phase immunological method, (see, for example, Broome, S., and Gilbert, W., (1978), Proc. Natl. Acad. Sci. U.S.A., 75, 2746–2749). Briefly, small cultures of individual colonies were grown, harvested and lysed using lysozyme and "Triton (Registered Trade Mark) X-100." ("Triton X-100" is iso-octylphenoxypolyethoxyethanol, a non-ionic detergent).

Any HA sequences present were bound to a polystyrene tube coated with FPV-HA specific IgG. Bound antigen was then specifically labelled with high specific activity $125_{I\text{-}IgG}$.

Immune reactivity was detected in all colonies containing an FPV-HA gene insert; those colonies containing only the parent pWT121 plasmid showed no activity (see following Table).

| Radioimmunoassay of FPV—HA in lysates of bacteria containing pWT121/FPV plasmids | | | |
|---|---|---|---|
| Colony No. | HA content (ng/50 μl) | Phenotype | Insert |
| 2 | >20 | $Tc^r$ | A |
| 5 | 0 | $Tc^r$ | — |
| 6 | >20 | $Tc^r$ | A |
| 8 | 0 | $Tc^r$ | — |
| 11 | >20 | $Tc^r$ | A |
| 13 | 0 | $Tc^r$ | — |
| 14 | 0 | $Tc^r$ | — |
| 15 | >20 | $Tc^r$ | A |
| 16 | >20 | $Tc^r$ | A |

As indicated above, immune reactivity was detected in all colonies containing an FPV-HA gene insert (A); those colonies containing only the parent pWT121 plasmid showed no activity.

In the case of the so-called pWT series of expression plasmids, as with pBR322, there is the possibility that, under the appropriate conditions, these normally mobilisation minus (mob−) plasmids may be mobilised (i.e. transferred from one bacteria to another). It has recently been shown, (see, for example, Twigg, A. J. and Sherratt, D. J. (1980), Nature, 283, 216–218), that, although the DNA coding for the Col El mobility protein(s) is absent from pBR322, this protein may nevertheless induce mobility by transcomplementation when present in the same cell on a compatible plasmid, such as Col K.

The site of binding to the plasmid DNA of the mobility protein(s) has been shown to be the so-called "nic site" or "transfer origin", (see, for example, Warren G. J., et al, (1978), Nature, 274, 259–261). For example, in pBR322, this site maps in the 622 bp Hae II B fragment. Mutations in the mobility gene are mob−. However, they may be complemented by mob+ Col El derivatives or related plasmids, implying a trans-acting protein.

(Col El type plasmids are non-conjugative, but are mobilised when a sex factor, such as an F' or R factor, is introduced into the cell. The mobilisation of a nic+, but mob− plasmid, such as pBR322, therefore requires the presence of two other plasmids, viz a sex factor and a compatible Col El type mob+ plasmid).

The nic site is specifically required for mobilisation and plasmids minus this site cannot be complemented.

Thus, although, pBR322 and the pWT series plasmids do not contain all of the mobility genes, they all contain the nic site and hence may be complemented for mobility. In order to produce safer, non-mobile vectors, it is desirable to remove the nic site. For example, this may be accomplished by deleting a Hae II fragment.

Figure 13:
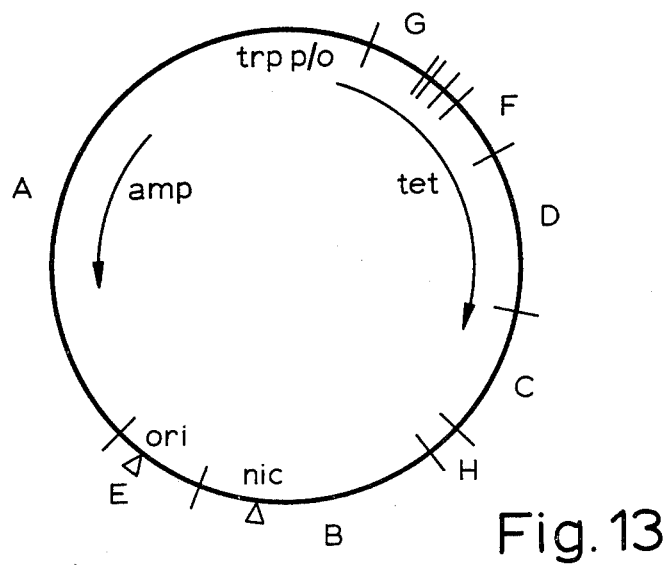

The nic site may be removed from the plasmids pWT 111, 121 and 131 in the following manner:

Consideration of the Hae II restriction maps of the above plasmids indicates that only two fragments (B and H) may be removed and still leave the ampicillin and tetracycline genes, the tryptophan promoter and the origin of replication. Reference may be made in this connection to FIG. 13 of the accompanying drawings.

Fragment B is 622 bp and fragment H is 83 bp. Therefore, nic− plasmids (minus B and H) are lacking 705 bp. Of course, this must be taken into account in the characterisation of the nic− derivatives of the above plasmids. For example, in pWT111 (nic−), the Pst I site is 2253 bp from the Sal I site.

The nic− derivatives of pWT111, 121, and 131 are termed pWT211, 221 and 231, respectively.

The first step in this illustrative procedure is to partially digest the plasmid such that each molecule is cleaved, on average, 2 or 3 times. The digests are then religated using $T_4$ DNA ligase and the ligated DNA is transformed into E. coli K 12, e.g. HB101. Transformants are selected on ampicillin and tetracycline using minimal agar plates to induce trp transcription and ensure tetracycline resistance.

The resulting colonies will contain the recircularised starting plasmids, as well as examples lacking one or both of the Hae II fragments. The latter may be identified by screening single colonies and looking for plasmids smaller than the parental plasmid. Prospective nic− derivatives may be confirmed by restriction enzyme analysis of purified plasmid DNA.

Figure 14:
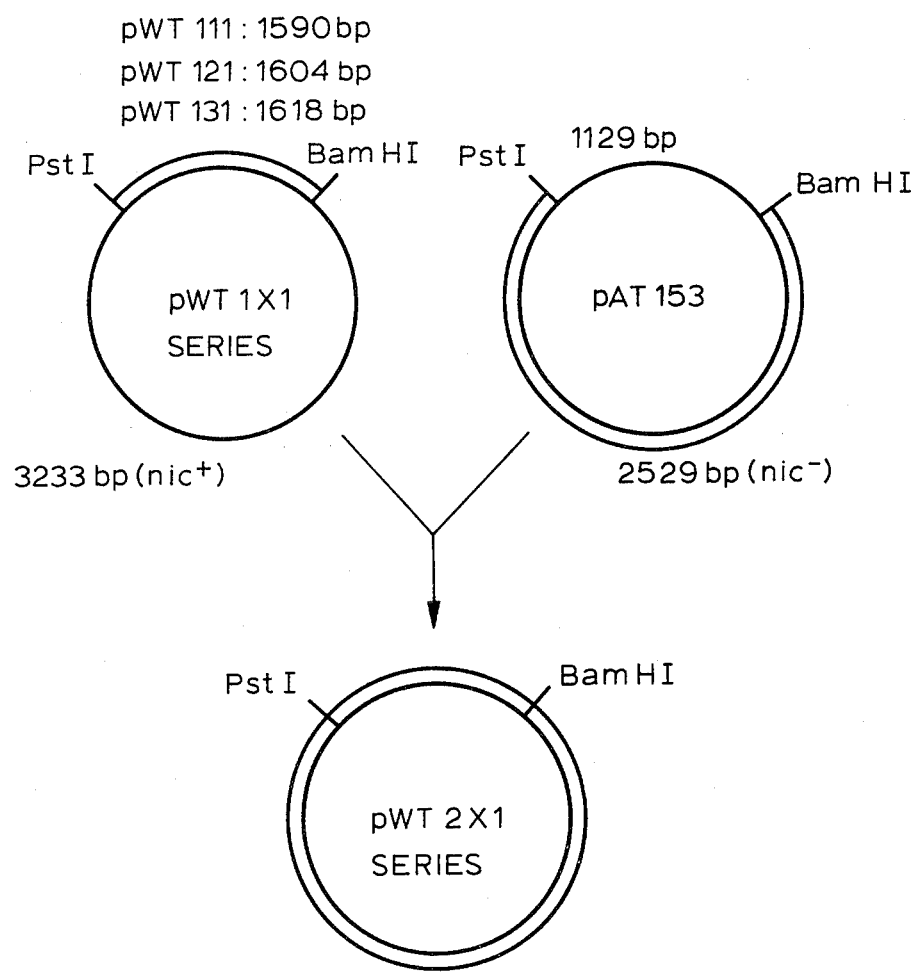
Figure 15:
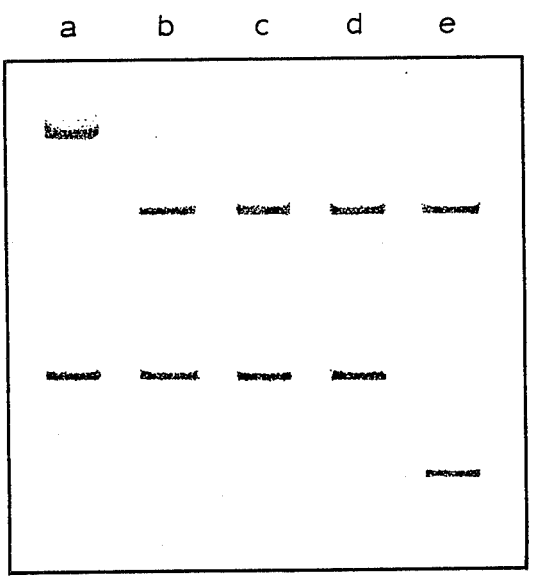
Figure 16:
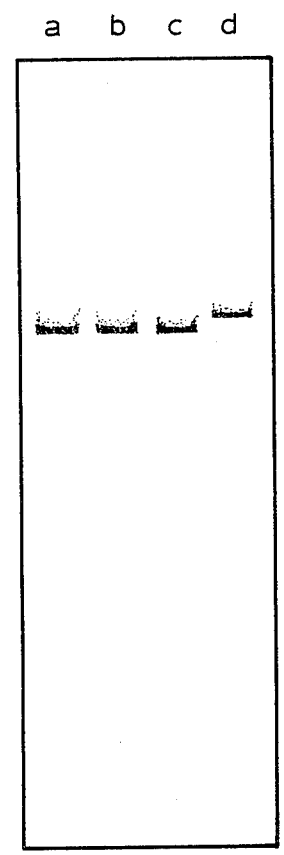
Figure 17:
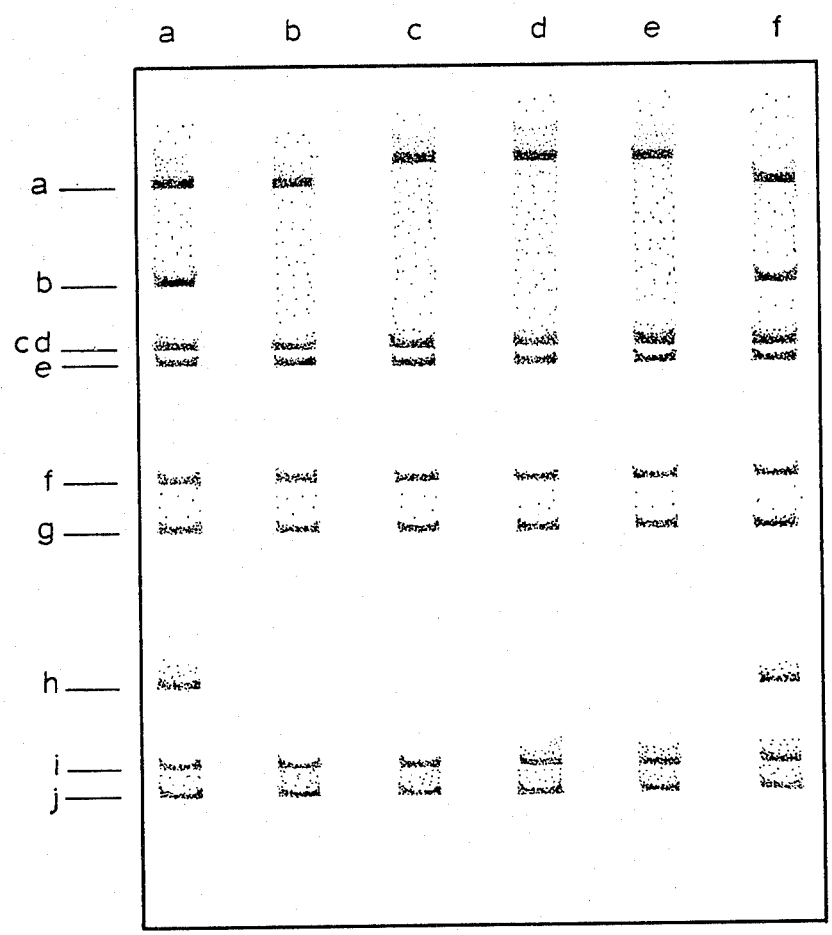

Instead of using the above illustrative procedure involving partial restrictions necessitating the screening of, perhaps, hundreds of colonies, it is generally more convenient to construct the nic− derivatives as outlined in FIG. 14 of the accompanying drawings.

Briefly, the pWT plasmids are restricted with Pst I and Bam HI and bands containing the trp p/o region are isolated from polyacrylamide gels. The plasmid pAT153 (nic−) is restricted with Pst I and Bam HI and the band of 2531 bp is isolated from a polyacrylamide gel. The former bands are ligated individually with the latter band using $T_4$ DNA ligase and the ligated material is used to transform E. coli HB 101. DNA from single colonies may be isolated and the structure thereof confirmed by restriction enzyme analysis, e.g. Hae II digests of pAT153, pWT series and pWT (nic−) series.

In other words, the nic− derivatives may be constructed by substituting the region in the pWT plasmids bounded by the Pst I and Bam HI sites containing the origin of replication and the nic site with the corresponding region from pAT153, which is a deletion derivative of pBR322 and is lacking the 622 bp Hae II B fragment and adjacent 83 bp Hae II H fragment.

The following further illustrates the present invention:

Preparation of pEH3, pEH4 and pEH5:

Cultures of E. coli K12 strain HB101, (see, for example, Boyer, H., et al, (1969), J. Mol. Biol., 41, 459–472), containing the plasmid pBR322 were grown either in L-broth or in M9 salts, glucose, casamino acids medium, (see, for example, Miller, J. H., Experiments in Molecular Genetics, Appendix 1, Cold Spring Harbor Laboratory, N.Y., (1972), 431–435). At an $A_{600}$ of 0.6, chloramphenicol was added to plasmid cultures to a final concentration of 150 μg/ml and incubation continued for 16 hours at 37° C. DNA was isolated from cell lysates by centrifuging in CsCl/ethidium bromide gradients, (see, for example, Katz, L., et al, (1973), J. Bacteriol, 114, 577–591; and Wensink, P.C., et al, (1974), Cell, 3, 315–325). DNA bands were removed by side puncture with a 1 ml syringe and 16 G needle under illumination from 366 nm u.v. light and ethidium bromide was removed by passage through "Dowex (Registered Trade Mark) AG50" (acidic cation exchange resin).

All DNA solutions were dialysed against TE buffer (10 mM Tris, 1 mM EDTA pH 7.5) to remove excess CsCl, concentrated by ethanol precipitation and stored at −70° C.

The DNA mixture obtained was limited digested with Hind III as follows:

2 μg of pBR322 were incubated with 5 units of Hind III in a buffer containing 50 mM Tris-HCl pH 7.5, 50 mM NaCl, 10 mM $MgCl_2$, 5 mM β-mercaptoethanol and 2 mM dithiothreitol. Incubation was at 37° C. for 90 minutes in a volume of 40 μl. The reaction was then terminated by a 5 minute incubation at 65° C.

Isolation of the Hind III trp E fragment

20 μg of pRH1/trpE was limit digested with Hind III, electrophoresed on 1% agarose gels and the band containing linear trpE removed. The trpE fragment was recovered from the gel slice by electrophoresis into a dialysis sac, followed by phenol extraction and ethanol precipitation.

Ligation

Ligase incubations contained 0.2 μg of the trpE fragment, 0.4 μg of the Hind III restricted pBR322 and 0.1 units of $T_4$ polynucleotide ligase per 20 μl of reaction buffer. The reaction mixture was incubated for 4 hours at 16° C.

Transformation 0.01 μg of the ligated DNA were used to transform E. coli W3110 trp o E∇1 strain.

Ampicillin-resistant recombinants capable of complementing these trpE− cells were selected. $1.2 \times 10^4$ amp-r colonies able to grow in the absence of tryptophan were obtained per μg of plasmid DNA.

Fifty of these colonies were selected at random and transferred using tooth-picks onto minimal agar plates, (see, for example, Miller J. H., loc cit), containing 100 μg/ml ampicillin and 12.5 μg/ml tetracycline. Thirty-one of the fifty colonies grew after overnight incubation, indicating the presence of a tetracycline resistance protein in this population.

Plasmid DNA was isolated from representative colonies of the tetracycline-sensitive and-resistant groups and the Hind III fragment patterns analysed by gel electrophoresis on 1% agarose gels. Plasmid DNA from all the ampicillin-resistant, trp+ clones contained the parent pBR322 DNA of Mr $2.8 \times 10^6$ (4.361 kb) and the E. coli Hind III trpE fragment of Mr $3.5 \times 10^6$ (5.350 kb). The plasmids produced were subjected to the following further procedures to confirm the structure thereof.

Orientation of the trpE fragment

One consequence of religating Hind III digests of pBR322 with the trpE fragment is that the trpE fragment may be inserted in one of two different orientations. It may be such that transcription from the trp promoter proceeds through the tet-gene of the plasmid or away from the tet-gene. The orientation of the tet-resistant plasmid (pEH3) and tet-sensitive plasmid (pEH4) was determined in the light, (see, for example, Bennett, M. E., et al, (1976), Proc. Natl. Acad. Sci.

Figure 7:
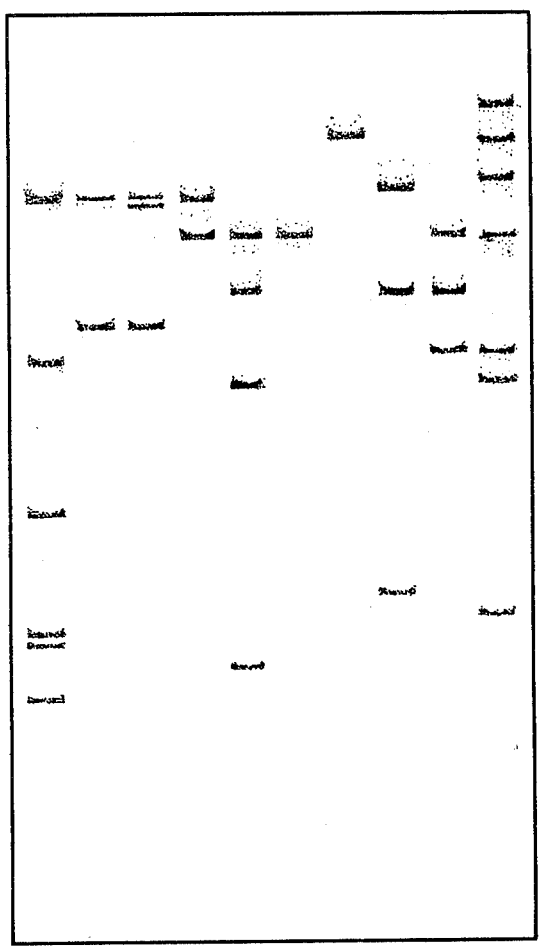

U.S.A., 73, 2351-2355), of existing Hpa I sites in the trp E fragment and Bam HI sites in pBR322, (see, for example, Bolivar, F., et al, loc cit). FIG. 7 of the accompanying drawings illustrates the results of limit digestions of plasmids pBR322, pEH3 and pEH4 with either Hind III, Hpa I (EC 3.1.23.23), Bam HI (EC 3.1.23.6) or a combination of these enzymes.

(Accompanying FIG. 7 illustrates an agarose gel showing the restriction endonuclease sites for Hpa I, Hind III and Bam HI in pEH3 and pEH4 and the orientation of the cloned trpE DNA in these plasmids. The tracks a to j contain the following DNAs with sizes in kilobase pairs (kb):- (a) PM2 DNA digested with Hind III as size markers. Visible bands are 1 to 6 of size 5.4, 2.35, 1.05, 0.475, 0.45 and 0.27 kb, respectively. (j) λc.I857,S7 DNA digested with Hind III as size markers. Bands visible are A to G of size 21.79, 9.38, 6.30, 4.20, 2.38, 2.11 and 0.47 kb, respectively. (b) Super-coiled pBR322 DNA. (c) pBR322 incubated with Hpa I. (d) pEH3 digested with Hind III. (e) pEH3 digested with Hind III and Hpa I. Bands measure 4.3, 3.25, 1.95 and 0.30 kb. (f) pBR322 digested with Bam HI. (g) pEH3 digested with Bam HI. (h) pEH4 digested with BAm HI and Hpa I. Complete digest fragments measure 5.7, 3.25 and 0.67 kb. (i) pEH3 digested with Bam HI and Hpa I. Complete digest fragments measure 4.3, 3.25 and 2.4 kb.) There are no Hpa I sites in pBR322 (compare lanes b and c) and no Bam HI sites in trpE (compare lanes f and g). When restricted with Hind III alone, both pEH3 and pEH4 give linear pBR322 and trpE fragments (lane d). Double digests of pEH3 and pEH4 with Hind III and Hpa I also give identical profiles (lane e). In this case, linear pBR322 (4.360 kb) is regenerated along with three other fragments. of 3250, 1950, and 305 bp. Since pBR322 has no Hpa I targets, (see, for example, Bolivar, F., et al, loc cit), it is concluded that there are two Hpa I targets in the trpE fragment. One has already been reported and is in the promoter region (see, for example, Bennett, M. E., et al, loc cit), the second site is approximately 300 bp from one of the Hind III sites.

Double digests with Bam HI and Hpa I were used to determine the orientation of the trpE fragment and the position of the second Hpa I site. The fragments produced are shown in lane h for pEH4 and in lane i for pEH3. It is clear that these plasmids contain trpE fragments in different orientations. The size of the smallest fragment derived from pEH4 is more easily estimated from the results illustrated in FIG. 8 of the accompanying drawings. This Figure shows the small fragments derived by restriction digests of pEH3, pEH4 and pBR322 with Sal I (EC 3.1.23.27), Bam HI, Hpa I, Eco RI and Hind III.

Figure 8:
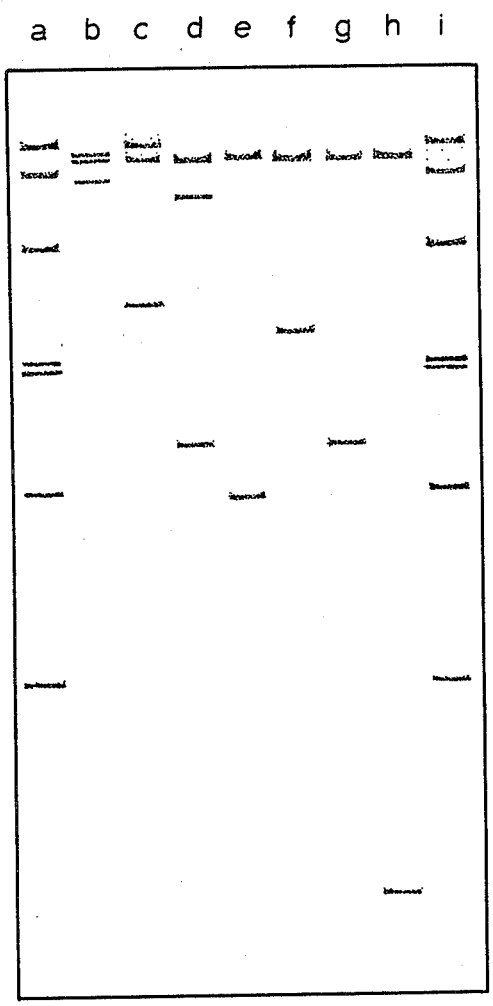

(Accompanying FIG. 8 illustrates a 5% acrylamide gel showing low molecular weight DNA fragments from pBR322, pEH3 and pEH4 after digestion with Hpa I, Bam HI, Hind III and Sal I restriction endonucleases. The tracks a to i contain the following DNAs with sizes in base pairs (bp):- (a,i) PM2 DNA digested with Hind III as size markers. Bands 1 to 7 are of size 5400, 2350, 1050, 475, 450, 270 and 110 bp, respectively. (b) pEH3 digested with Bam HI and Hpa I. (c) pEH4 digested with Bam HI and Hpa I. Smallest band estimated as 640 bp. (d) pEH3 digested with Hind III and Hpa I. Smallest band estimated as 295 bp. (e) pBR322 digested with Bam HI and Sal I. Smallest band estimated as 275 bp. (f) pBR322 digested with Hind III and Sal I. Smallest band estimated as 620 bp. (g) pBR322 digested with Bam HI and Hind III. Smallest band estimated as 350 bp. (h) pBR322 digested with Eco RI and Hind III. Smallest band estimated as 25 bp.)

From the above results, the restriction maps for pEH3 and pEH4 illustrated in FIGS. 2 and 3 of the accompanying drawings have been constructed. That the second Hpa I site lies "upstream" from the trp promoter is based on known sizes of the trpE protein, anthranilate synthetase, and the trpD gene fragment contained in the Hind III trp E fragment. Anthranilate synthetase is a protein of 60,000 daltons, (see, for example, Ito, J., et al, (1969), J. Bacteriol, 97, 725–733), (approximately 500 amino acids), while only about 1/6 of the trpD protein gene, (equivalent to ~275 bp), is specified by this Hind III fragment, (see, for example, Hopkins, A. S., et al, (1976), J. Mol Biol., 107, 549–569). Thus, a DNA length of approximately 1800 bp is required to specify these polypeptides. In addition, there are 162 bases in the leader sequence at the 5'-end of trp mRNA and a further 11 bases from the start of trp mRNA to the Hpa I target in the trp promoter, (see, for example, Lee, F., et al, (1978), J. Mol. Biol, 121, 193–217). This total of 1948 bp between Hpa I and Hind III is in good agreement with the Hpa I - Hind III distance of 1950 bp derived from gel analysis and is consistent with the conclusion that the second Hpa I site is "upstream" from the trp promoter.

Control of tetracycline sensitivity from the trp promoter

Placing the small Hpa I-HInd III fragment "upstream" from the trp promoter, unambiguously indicates that, in the tetracycline-resistant group of plasmids (pEH3), transcription from the trp promoter is directed towards the tetracycline gene, while, in the tetracycline-sensitive plasmid (pEH4), the opposite is true. On this basis, it would be expected that expression of the tetracycline gene in pEH3 is controlled from the trp promoter and that any insertion into the Hind III site of pBR322 destroys the tetracycline promoter.

This has been tested by examining the tetracycline resistance of E. coli containing pEH3 grown in the presence and absence of tryptophan, i.e. under conditions where the trp genes should either be repressed or derepressed. Plasmid pEH3 in strain W3110 trp o E∇1 was grown on a medium containing M9 salts, glucose, casamino acids and 5 µg/ml tetracycline. At an A$_{600}$ of 0.05, the culture was split and 200 µg/ml of tryptophan was added to one half. After incubation for a further hour, the cells were diluted and plated onto agar plates containing increasing concentrations of tetracycline. Those cells grown for 1 hour on 200 µg/ml tryptophan were grown on minimal agar plates supplemented with tryptophan.

Figure 9:
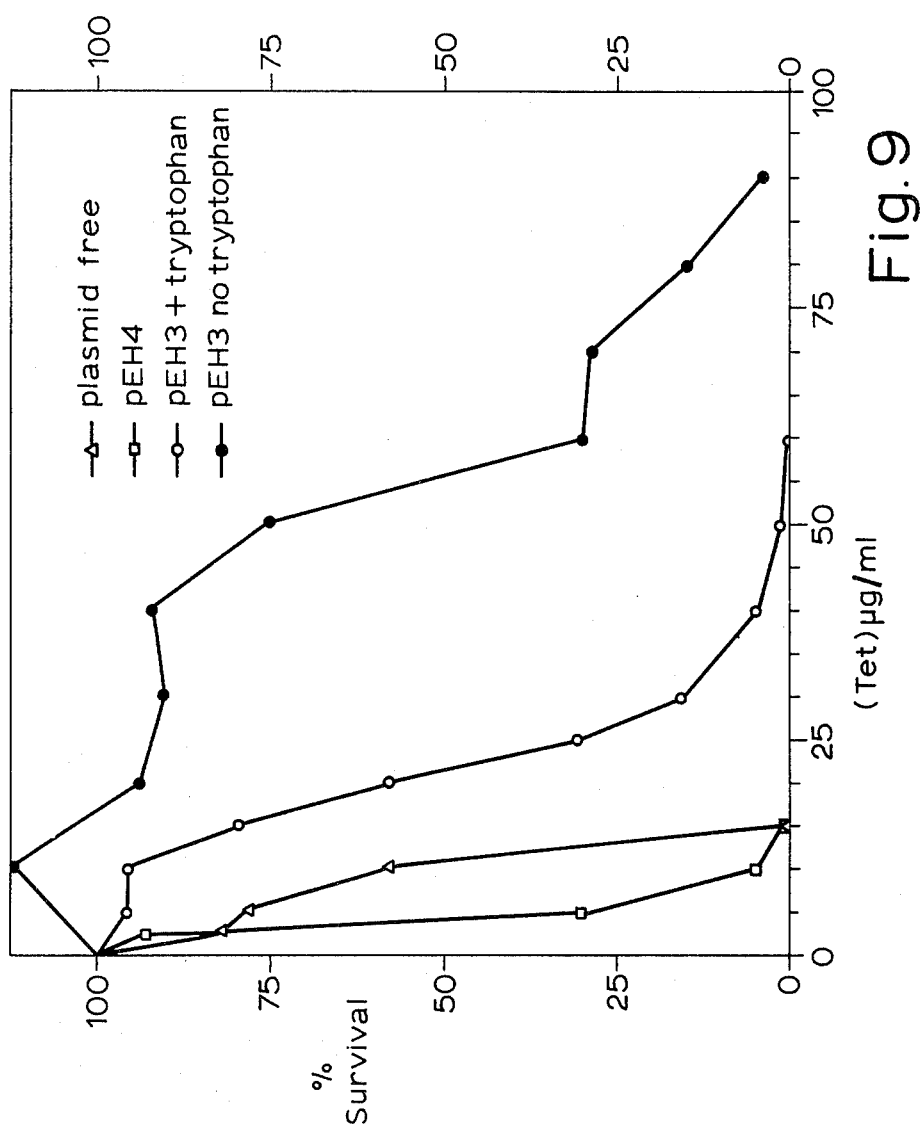

The results of this series of experiments are illustrated in FIG. 9 of the accompanying drawings.

(Accompanying FIG. 9 illustrates the efficiency of plating of the trp o E∇1 strain and its derivatives on increasing concentrations of tetracycline. Cultures of the trp o E∇1 strain containing the indicated plasmids were grown in defined media and treated as described below. % survival was determined relative to the appropriate plate containing no tetracycline. Plates containing 80–400 colonies were used to determine the % survivors. The following tetracycline concentrations, capable of killing 50% of the cells as determined by the colony assay (EOP 50%), were measured from the Figure: 12 µg/ml for plasmid free cells; 4.5 µg/ml for pEH4 containing cells; 23 µg/ml for pEH3 containing cells pre-incubated with 200 µg/ml tryptophan; 56

μg/ml for pEH3 containing cells grown without tryptophan). The presence of tryptophan in the medium caused a 2.5-fold decrease in tetracycline resistance mediated by pEH3. Similar experiments with pEH4 and with plasmid-free W3110 trp o E∇1 (where the initial growth medium contained no tetracycline) showed that these bacteria were sensitive to very low concentrations of tetracycline.

The Hind III site proximal to the Eco RI site of pEH3 was deleted as follows to produce the plasmid pEH5.

20 μg of pEH3 prepared as described above were digested with Eco RI, gel filtered on "Sephadex (Registered Trade Mark) G-50" (bead-form cross-linked dextran gel) in 50 mM NaCl/0.1% W/V SDS and the excluded DNA peak concentrated by ethanol precipitation and dissolved in water.

The linear Eco RI digested pEH3 was digested with exonuclease III at 20° C. The mixture contained 10 μg linear plasmid, 60 mM Tris pH 8, 0.66 mM $MgCl_2$, 4 mM dithiothreitol and 40 units of exonuclease III in a total volume of 200 μl. 100 μl aliquots (5 μg) were removed after 5 and 10 minutes, extracted with phenol and chloroform and ethanol precipitated.

Exonuclease III treated plasmid (5 μg) was treated with S1 nuclease for 15 minutes at 30° C. in a volume of 100 μl to produce blunt ends. The reaction contained 150 mM NaCl, 25 mM sodium acetate pH 4.6, 0.1 mM $ZnSO_4$, DNA and 2.5 units of S1 nuclease. Following incubation, the mixture was extracted with phenol and chloroform and then precipitated with ethanol. 3 μg of the S1 digested DNA were ligated in a final volume of 10 μl with 1 μl $T_4$ DNA ligase (0.8 units) at 15° C. for 16 hours and then at 4° C. for 24 hours.

Figure 10:
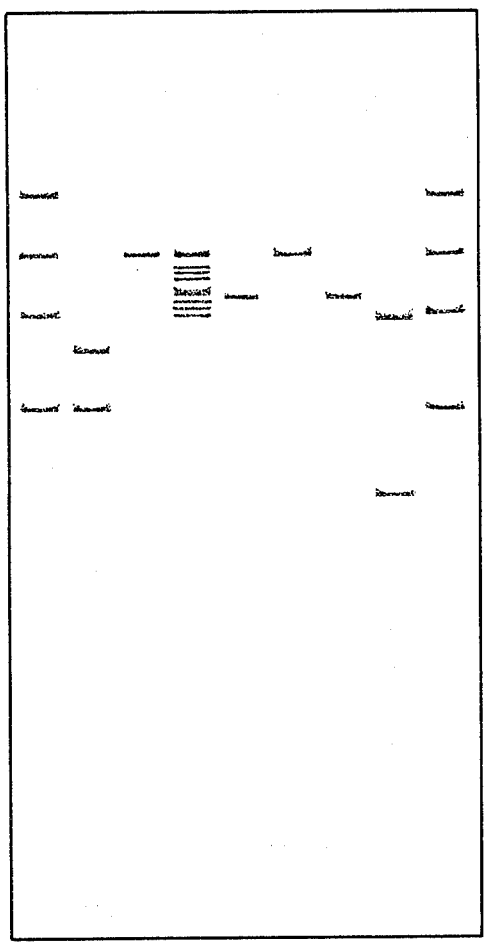

(FIG. 10 of the accompanying drawings illustrates a 1% agarose gel showing deletion of Hind III and Hpa I sites from pEH3.

The tracks a to i contain the following DNAs with sizes in kilobase pairs (kb): (a,i) λ cI857,S7 digested with Hind III as size markers. Bands visible in agarose are A to F of size 21.79, 9.38, 6.30 and 4.20 kb, respectively; (b) pEH3 digested with Hind III; (c) pEH3 digested with Sal I; (d) pooled colonies digested with Hind III (e) pEH5 digested with Hind III, (f) pEH505 digested with Hind III (g) pEH5 digested with Hpa I; (h) pEH505 digested with Hpa I.)

Preparation of plasmids of the pWT series
Bacteria and plasmids

The bacterial strains used were both *Escherichia coli* K12 derivatives; KB101 F− pro leu thi lac Y str$^r$ rk− mk− Endo 1− rec A− & ED8689 trpR− rk− mk+.
Media and transformation Cultures were grown in M9 salts, glucose, casamino acids medium, (see, for example, Miller, J. H., loc cit), for plasmid DNA preparations and tetracycline sensitivity testing. For plasmid-containing strains, antibiotics were added at the appropriate concentration. Cells to be used for transformation were grown in L-broth.

Throughout the tetracycline sensitivity testing, cells were plated on M9, glucose, casamino acids minimal agar supplemented with tetracycline (0 to 80 μg/ml), 3β-indole acrylic acid (20 μg/ml) or tryptophan (100 μg/ml) where indicated.

The transformation protocol followed was that of Glover (loc cit). Cells were plated on either nutrient agar no. 2 supplemented with ampicillin (100 μg/ml) or on M9, glucose, casamino acids minimal agar supplemented with ampicillin (100 μg/ml) or tetracycline (10 μg/ml).

Preparation of plasmid DNA
Plasmid DNA was prepared either as described for pEH5 above or by phenol/chloroform extractions of cleared lysates, followed by isopropanol precipitation of the DNA and final resuspension in TE buffer (10 mM Tris-HCl pH 7.5, 1 mM EDTA).

Enzyme reactions
Restriction endonuclease digests:

DNA restriction digests were performed in either a high or low salt buffer system at 37° C. for 2 hours, the reaction volume varying from 10 to 200 μl and the amount of enzyme added from 1 to 20 units per μg plasmid DNA. Bam HI, Eco RI, Hha I (EC 3.1.23.19), Hind III and Pst I (EC 3.1.23.31) digests were carried out in 10 mM Tris-HCl pH 7.5, 10 mM $MgCl_2$, 50 mM NaCl, 1 mM dithiothreitol, 100 μg/ml gelatin. For Hpa I digests, the reaction mixture differed only in that 50 mM NaCl was replaced by 5 mM NaCl. Hinf I worked equally well in both reaction mixtures.

Where plasmid DNA not prepared by the caesium chloride/ethidium bromide method was being digested, the reaction mixture also contained ribonuclease type I-A (heat treated for 10 minutes at 95° C. to remove any DNAase activity) at 50 μg/ml, to remove RNA that co-precipitated with the DNA on purification.

All reactions were terminated by heating to 65° C. for 5 minutes.

Ligations:
Cohesive end ligations were performed at volumes of 10 to 20 μl in 50 mM Tris-HCl pH 7.8, 10 mM $MgCl_2$, 20 mM dithiothreitol, 1 mM ATP using 0.01 to 0.02 units of ligase for 0.5 to 3 μg of DNA. Reactions were incubated overnight at 15° C. For blunt end ligations, the same reaction mixture was used, but the ligase was increased to 0.2 to 0.6 units for 1 to 3 μg of DNA and incubation temperature increased to 25° C.

DNA polymerase I filling of 5' extensions:
0.5 to 3.5 μg of DNA were polymerase filled in 50 mM Tris-HCl pH 7.8, 10 mM $MgCl_2$, 1 mM β-mercaptoethanol, 0.1 mM each of dATP, dCTP, dGTP, dTTP in a volume of 50 μl using 0.25 to 1.5 units of polymerase. The mixture was incubated for 10 minutes at 10° C., after which an aliquot could be used directly for blunt end ligation or the whole phenol/chloroform extracted and then ethanol precipitated.

Polynucleotide kinasing of Hind III linker DNA:
2.5 μg of decamer Hind III linker were kinased for 60 minutes at 37° C. with 10 units of kinase in 25 mM Tris-HCl pH 7.8, 5 mM $MgCl_2$, 0.125 mM ATP, 25 μg/ml bovine serum albumin. The 5' termini were also labelled by adding 100 μCi [γ−$^{32}$P] ATP (3000 Ci/mmol) to the reaction. The reaction was terminated by the addition of SDS to 0.1% W/V and EDTA to 10 mM and the whole chromatographed on a 30×0.7 cm column of "Sephadex G-50" (SF) equilibrated in 50 mM NaCl/0.1% W/V SDS. The excluded fractions were pooled, ethanol precipitated and resuspended in water to 50 μg/ml.

Bacterial alkaline phosphatase treatment of Hind III restricted pBR322: 5 to 10 μg of linearised pBR322 in 20 mM Tris-HCl pH 7.5, 0.1% W/V SDS were treated with 5 μg of bacterial alkaline phosphatase for 60 minutes at 37° C. This was then phenol/chloroform extracted and the DNA ethanol precipitated.

Exonuclease III and S1 nuclease digestion of Eco RI restricted pWT101:
The conditions used were as described for the deletion of the Hind III site in pEH3, except that aliquots (3.33 μg) were removed after 1, 3 and 5 minutes of exonuclease III digestion.

Preparation of gel samples from whole cell lysates

For 'whole cell lysis' agarose gels, a representative sample of plasmid containing cells was scooped from a culture plate using a plastic sterile loop and resuspended in 200 μl of agarose electrophoresis buffer. To this was added 50 μl of "Ficoll" buffer (5% W/V SDS, 10% W/V Ficoll (copolymer of sucrose and epichlorohydrin), 0.06% W/V bromophenol blue) and the mixture incubated at 65° C. for 30 minutes to lyse the cells and then vortexed for 1 minute. About 40 μl of such a sample was found sufficient for plasmid identification. RNA present with the DNA could be removed by either adding ribonuclease to 50 μg/ml to the sample, followed by a 30 minute incubation at 37° C., or added directly to the agarose gel matrix to 1 μg/ml. Both methods remove the RNA smear which would otherwise be present on the gel.

Gel Electrophoresis

Agarose gels (20×15×0.5 cm) of 0.8 to 1.4% composition were run under conventional conditions. Gels were either electrophoresed at 40 volts overnight or for 3 hours at 120 volts and then stained and photographed.

Acrylamide gels (20×15×0.15 cm) of 5 to 10% composition were used to identify small restriction fragments. Staining and photography were as for agarose gels.

Isolation of the tryptophan promoter-operator Hinf I fragment and attachment of Hind III linker 6 μg of pEH5 were Hinf I restricted and electrophoresed on a 5% W/V acrylamide gel, after which the 497 bp Hinf I tryptophan promoter-operator and comigrating pBR322 band were cut from the gel and the DNA extracted in known manner.

The Hinf I ends were then DNA polymerase I filled and Hind III linker attached to them by blunt end ligation at a ratio of 50 linker fragments per Hinf I fragment (this reduces the possibility of Hinf I fragments self-ligating). Sticky ends were produced by restricting the mixture with Hind III, the DNA ethanol precipitated, resuspended in 50 μl of 50 mM NaCl, 0.1% W/V SDS, and the whole chromatographed on a 50×0.7 cm column of "G150 Sephadex" (pre-equilibrated with 50 mM NaCl, 0.1% W/V SDS). The excluded peak was pooled and the DNA ethanol precipitated.

Construction of pWT101

The complete *E. coli* tryptophan promoter, operator, leader sequence and the first seven amino acids of trpE are contained on a Hinf I fragment of approximately 497 bp present in pEH5. The 497 bp Hinf I fragment was cloned into the Hind III site of pBR322 with the aid of decamer Hind III linker DNA. To undertake this meant that the Hinf I ends had first to be filled in with DNA polymerase I to allow attachment of linker DNA. The fragment was then ligated to bacterial alkaline phosphatase treated Hind III cut pBR322 and the mixture used to transform *E. coli* HB101 applying a nutrient agar ampicillin selection. A total of 582 colonies was obtained from the transformation.

Cloning into the Hind III site of pBR322 inactivates the tetracycline promoter, thereby rendering any transformant tetracycline-sensitive unless the cloned piece has its own promoter transcribing into the tetracycline genes. As the Hinf I fragment contains the tryptophan promoter-operator region, transformants containing a plasmid with the fragment cloned in the correct orientation, i.e. transcribing towards the tetracycline promoter, should be tetracycline-resistant. To test this, forty-eight colonies randomly chosen from the ampicillin transformation plates were stabbed out onto M9 casamino acids minimal agar plates supplemented with tetracycline (10 μg/ml). Of these, eleven were found to be tetracycline-resistant, which is the expected figure as with two fragments present there was a one-in-four possibility of obtaining the correct orientation.

The presence of inserted DNA was also confirmed by picking colonies from both sets of plates and testing against a pBR322 control by running whole cell agarose gels. By these methods, ampicillin resistant and ampicillin, tetracycline resistant colonies which contained plasmids with inserted DNA were isolated. Plasmid DNAs were prepared from a number of these colonies for restriction endonuclease analysis.

Figure 11:
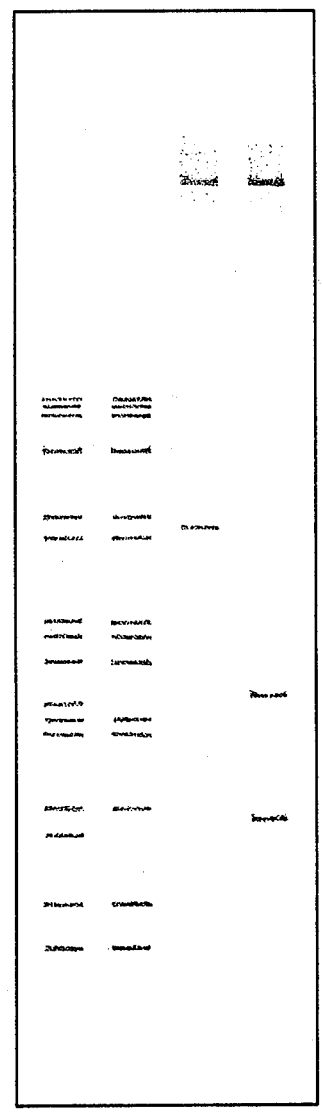

FIG. 11 of the accompanying drawings illustrates the production and characterisation of pWT101 and may be interpreted as follows:
 (a) pEH5 digested with Hinf I and Hpa I;
 (b) pEH5 digested with Hinf I alone;
 (c) pWT101 digested with Hind III;
 (d) pWT101 digested with Hind III and Hpa I.

Construction of pWT111

Removal of the Hind III site distal to the tryptophan promoter

The distal Hind III site was deleted by Eco RI cleavage, followed by removal of DNA by exonuclease III and S1 nuclease digestion. A DNA polymerase I step was also included prior to ligation so as to fill in any asymmetrical ends left after S1 nuclease digestion.

Digestion times of 1, 3 and 5 minutes were chosen.

The three DNA mixtures after Eco RI restriction, exonuclease III digestion (1, 3 and 5 minutes), DNA polymerase I filling and blunt end ligation were used to transform HB101 cells. A double antibiotic selection was employed by plating on M9, casamino acids minimal agar supplemented with ampicillin and tetracycline; the double selection ensuring that the β-lactamase and tetracycline genes remained intact.

For further characterisation of the probable deletants, two transformants each from the 1 and 5 minute fractions and four from the 3 minute fraction were selected.

Characterisation of the deletant plasmids

None of the eight plasmids produces a 512 bp fragment when cut with Hind III and all migrate to a position above the 4.36 kb fragment of Hind III restricted pWT101. All plasmids were double digested with Hpa I and Pst I, so producing two fragments, the smaller of which spans the area concerned (the region about the Eco RI site in pWT101). The sizes of the fragments generated in pWT101 are 3777 and 1096 bp. Examination clearly illustrated the fact that the latter fragment had been deleted into in every case, while the former, as expected, has remained unaltered. The amounts of DNA deleted range from 51 bp in pWT111 (1 minute exonuclease III digestion) to 361 bp in pWT118 (5 minutes exonuclease III digestion).

As pWT111 has had the least amount of DNA deleted from it, and the tetracycline efficiency of plating results indicates that it is as efficient as pWT101 in transcription from the tryptophan promoter, it was chosen as the Hind III cloning vehicle to be used for translational phase changing.

Construction of pWT121

To change the phasing from the Hind III site of pWT111, the 5' extension was filled with DNA polymerase I and ligated on Hind III linker DNA, restricted with Hind III to remove excess linker and produce sticky ends and then religated. This added on 14 bp of DNA and altered the reading frame from the new Hind III site (the old site is now incomplete) by plus one nucleotide.

Construction of pWT131

The third reading frame, i.e. pWT111 plus 2 nucleotides, was obtained by repeating the same series of reactions on this phase changed plasmid. These plasmids, like pWT111, would produce small polypeptides which initiate at the start of trpE and terminate at stop codons (different ones in each case) preceding the tetracycline genes. However, because of the changes in reading frame, the polypeptides all have different C-terminal amino acid sequences although the N-terminal ones are the same.

Figure 12:
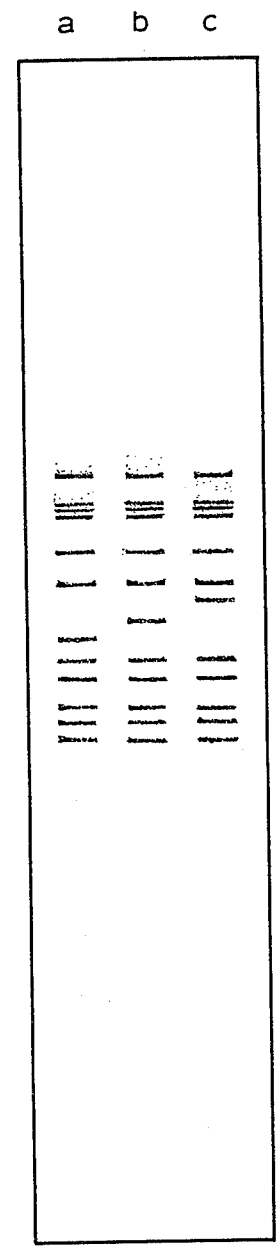

FIG. 12 of the accompanying drawings illustrates the changes occurring during the phase changing from pWT111 to pWT131. The Figure may be interpreted as follows:

(a) pWT111 digested with Hha I;
(b) pWT121 digested with Hha I;
(c) pWT131 digested with Hha I.

Preparation of pWT121/FPV and assay of gene expression of FPV-HA antigen

10 μg pWT121 were limit digested with Hind III. The resulting 5' terminal phosphates of the vectors were removed by treatment with 20 μg bacterial alkaline phosphatase for 30 minutes at 37° C. in a 25 μl incubation containing 20 mM Tris HCl pH 7.5 and 0.1% W/V SDS. After phenol extraction and ethanol precipitation, 0.2 μg DNA were ligated to ~40 ng FPV-HA gene in a 20 μl incubation containing 50 mM Tris-HCl pH 7.5, 10 mM $MgCl_2$, 20 mM dithiothreitol (DTT), 1 mM ATP and 0.02 units $T_4$ DNA ligase (New England Biolabs). After overnight incubation at 15° C., the mixtures were diluted to 100 μl with TCM (10 mM Tris-HCl pH 7.5, 10 mM $CaCl_2$, 10 mM $MgCl_2$) and used to transfect 200 μl $CaCl_2$—treated *E. coli* K12 HB101 by a known procedure. Transformants present after growth for 16 hours at 37° C. on L-agar plus 100 μg/ml carbenicillin (Pyopen, α-carboxy benzylpenicillin) were tested for tetracycline resistance by picking onto agar plates containing M9 salts, glucose and casamino acids plus carbenicillin and tetracycline (10 μg/ml).

Assay of gene expression

Liquid cultures (5 ml) of individual colonies were grown in M9 medium supplemented with β-indole acrylic acid (20 μg/ml) or tryptophan (100 μg/ml) where indicated. Cells were harvested by centrifugation, suspended in 0.3 ml cold 25% W/V sucrose/50 mM Tris pH 8 and incubated with 0.1 ml lysozyme (10 mg/ml). At 5 minute intervals, 0.1 ml 0.5 M EDTA and then 0.5 ml iced "Triton" solution were added (Triton solution is 60 mM EDTA, 50 mM Tris pH 8 and 0.1% V/V "Triton X-100"). This lysate was used for antigen assay without further treatment.

HA-antigen assays were performed in polystyrene culture tubes (Nunc No. 1410) using an antibody sandwich technique. Rabbit anti-FPV HA was purified by ammonium sulphate precipitation and DEAE-cellulose chromatography before use and labelled with $^{125}I$. Tubes were coated with 50 μl of 0.2 M $NaHCO_3$ pH 9 containing 60 μg/ml of purified, unlabelled IgG for 10 minutes at room temperature, washed with 3×1 ml aliquots of wash buffer and then incubated at room temperature either with known amounts (0.5–5 ng) of disrupted FPV or with the bacterial lysates. After 2 hours, the tubes were washed with 4×1 ml aliquots of wash buffer and finally incubated at 4° C. for 16 hours with 50 μl wash buffer containing 200,000 cpm $^{125}I$-anti HA. Tubes were again washed and counted in a Packard γ-counter. Antigen present was quantitated from standard curves relating the radioactivity bound to the amount of FPV present.

Preparation of $nic^-$ derivatives

Restriction of the three phase-changed pWT plasmids and pAT153 with both Bam HI and Pst I generates two fragments from each plasmid. This is illustrated in FIG. 14 of the accompanying drawings.

pAT153 produces fragments of 1129 bp and 2529 bp, the latter larger fragment containing the origin, but deleted for the nic site.

The pWT plasmids all produce the same 3233 bp fragment containing the origin and nic site, but different smaller fragments containing the trp control elements, the differences arising from the phase changing alterations at the Hind III site.

The plasmids were restricted with Pst I and Bam HI, electrophoresed on a 3.5% acrylamide gel and the pAT153 2529 bp, pWT111 1590 bp, pWT121 1604 bp and pWT131 1618 bp bands cut out and recovered from the acrylamide. The pAT153 band was then independently ligated to the three pWT bands and the ligation mixtures used to transform *E. coli* HB101 cells selected on nutrient agar containing carbenicillin at 100 μg/ml. As the pAT153 fragment is incapable of conferring resistance to ampicillin and tetracycline on its own and the pWT fragments lack an origin, selection on carbenicillin ensures that recombinant molecules obtained must contain these two fragments. Plasmid DNA's were prepared from a number of the colonies that grew on the transformation plates and these were used to confirm the presence of the desired plasmids by restriction analysis.

The following enzyme digests were performed:

Pst I and Bam HI digestion to generate the ligated fragments: Referring to FIG. 15 of the accompanying drawings, tracks b, c and d are digests of $nic^-$ derivatives of pWT131, 121 and 111, respectively. Track a is a digest of pWT131 and track e is a digest of pAT153. As is evident from the gel, all three $nic^-$ trp plasmids have acquired the pAT153 2529 bp fragment, but still retain the original trp control fragments.

Hind III digestion to demonstrate that trp p/o controlled expression site is still functional: Referring to FIG. 16 of the accompanying drawings, tracks a,b,c and d are digests of pWT231, 221, 211 and 131, respectively. All three $nic^-$ derivatives restrict with Hind III and are smaller than pWT131 due to the absence of the two Hae II fragments. Hae II digestion to demonstrate that the Hae II B and H fragments from the pBR322 region of the plasmids are absent: Referring to FIG. 17 of the accompanying drawings, tracks a to f are digests of pBR322, pAT153, pWT231, 221, 211 and 131, respectively. All four $nic^-$ plasmids (tracks b to e) are missing two Hae II fragments the 622 bp Hae II B and 82 bp Hae II H fragments of pBR322.

We claim:

1. A plasmid having an insertion site for a eukaryotic DNA fragment adjacent to a trp bacterial promoter, trp E gene and trp D gene, said insertion site being downstream from a prokaryotic ribosome binding site and the trp initiator codon such that the trp bacterial promoter controls transcription and translation of an inserted DNA fragment; the plasmid having a molecular length of 9866 bp; a Hind III site; a Bam I site 346 bp from the Hind III; a Sal I site 275 bp from the Bam I; an Eco RI site 3709 bp from the Sal I; a second Hind III site 31 bp from the Eco RI; a Hpa I site 305 bp from the second Hind III; a second Hpa I site 3250 bp from the first Hpa I and 1950 bp from the first Hind III; the trp promoter, the E gene and part of the D gene in the portion of 1950 bp between the second Hpa I and the first Hind III sites; a gene for tetracycline resistance immediately following the first Hind III site; and a gene for ampicillin resistance in the portion of 3709 bp between the Sal I and the Eco RI sites, the plasmid being referred to as pEH3; and the nic⁻ derivatives thereof.

2. A plasmid having an insertion site for a eukaryotic DNA fragment adjacent to a trp bacterial promoter, trp E gene and trp D gene, said insertion site being downstream from a prokaryotic ribosome binding site and the trp initiator codon such that the trp bacterial promoter controls transcription and translation of an inserted DNA fragment; the plasimid having a molecular length of 9866 bp; a Hind III site; a Bam I site 346 bp from the Hind III; a Sal I site 275 bp from the Bam I; an Eco RI site 3709 bp from the Sal I; a second Hind III site 31 bp from the Eco RI; a Hpa I site 1950 bp from the second Hind III site; a second Hpa I site 3250 bp from the first Hpa I and 305 bp from the first Hind III; the trp promoter, the E gene and part of the D gene in the portion of 1950 bp between the second Hind III and the first Hpa I sites; a gene for tetracycline resistance immediately following the first Hind III site and a gene for ampicillin resistance in the portion of 3709 bp between the Sal I and the Eco RI sites, the plasmid being referred to as pEH4, and the nic⁻ derivatives thereof.

3. A plasmid having an insertion site for a eukaryotic DNA fragment adjacent to a trp bacterial promoter, trp E gene and trp D gene, said insertion site being downstream from a prokaryotic ribosome binding site and the trp initiator codon such that the trp bacterial promoter controls transcription and translation of an inserted DNA fragment; the plasmid having a molecular length of 6750 bp; a Hind III site; a Bam HI site at 346 bp from the Hind III site; a Sal I site at 275 bp from the Bam HI site; a Hpa I site at 4230 bp from the Sal I site and 1950 bp from the Hind III site; the trp promoter, the E gene and part of the D gene in the portion of 1950 bp extending between the Hpa I site and the Hind III site; and a gene for ampicillin resistance in the portion of 4800 bp between the Hind III site and the Hpa I site, the plasmid being referred to as pEH5; and the nic⁻ derivatives thereof.

4. A plasmid having an insertion site for a eukaryotic DNA fragment adjacent to a trp bacterial promoter and trp E gene, said insertion site being downstream from a prokaryotic ribosome binding site and the trp initiator codon such that the trp bacterial promoter controls transcription and translation of an inserted DNA fragment; the plasmid having a molelcular length of 4874 bp; and Eco RI site; a Hind III site 31 bp from the Eco RI; a Hpa I site 313 bp from the Hind III; a second Hind III site 199 bp from the Hpa I; a Bam I site 346 bp from the second Hind III; a Sal I site 275 bp from the Bam I; a Pst I site 2958 bp from the Sal I and 752 bp from the Eco RI; a gene for tetracycline resistance extending from the region of the Hpa I site to beyond the Sal I site; a gene for ampicillin resistance in the region of the Pst I site; and the trp promoter and part of the E gene in the region between the Hpa I and the second Hind III site, the plasmid being referred to as pWT101; and the nic⁻ derivatives thereof.

5. A plasmid having an insertion site for a eukaryotic DNA fragment adjacent to the trp bacterial promoter and trp E gene, said insertion site being downstream from a prokaryotic ribosome binding site and the trp initiator codon such that the bacterial promoter controls transcription and translation of an inserted DNA fragment; the plasmid having a molecular length of 4823 bp; a Hpa I site; a Hind III site 199 bp from the Hpa I; a Bam I site 346 bp from the Hind III; a Sal I site 275 bp from the Bam I; a Pst I site 2958 bp from the Sal I and 1045 bp from the Hpa I; a gene for tetracycline resistance extending from the region of the Hpa I site to beyond the Sal I site; a gene for ampicillin resistance in the region of the Pst I site; and the trp promoter and part of the E gene in the region between the Hpa I and the Hind III sites, the plasmid being referred to as pWT111; and the nic⁻ derivatives thereof.

6. A plasmid having an insertion site for a eukaryotic DNA fragment adjacent to a trp bacterial promoter and trp E gene, said insertion site being downstream from a prokaryotic ribosome binding site and the trp initiator codon such that the trp bacterial promoter controls transcription and translation of an inserted DNA fragment; the plasmid having a molecular length of 4823 bp; a Hpa I site; a Hind III site 206 bp from the Hpa I; a Bam I site 353 bp from the Hind III; a Sal I site 275 bp from the Bam I; a Pst I site 2958 bp from the Sal I and 1045 bp from the Hpa I; a gene for tetracycline resistance extending from the region of the Hpa I site to beyond the Sal I site; a gene for ampicillin resistance in the region of the Pst I site; and the trp promoter and part of the E gene in the region between the Hpa I and the Hind III sites, the plasmid being referred to as pWT21 and the phasing from the trp promoter to the Hind III site being change 1 bp from the plasmid of claim 5; and the nic⁻ derivatives thereof.

7. A plasmid having an insertion site for a eukaryotic DNA fragment adjacent to a trp bacterial promoter and trp E gene, said insertion site being downstream from a prokaryotic ribosome bind site and the trp initiator codon such that the trp bacterial promoter controls transcription and translation of an inserted DNA fragment; the plasmid having a molecular length of 4851 bp; a Hpa I site; a Hind III site 213 bp from the Hpa I; a Bam I site 360 from the Hind III; a Sal I site 275 bp from the Bam I; a Pst I; site 2958 bp from the Sal I and 1045 bp from the Hpa I; a gene for tetracycline resistance extending from the region of the Hpa I site to beyond the Sal I site; a gene for ampicillin resistance in the region of the Pst I site and the trp promoter and part of the E gene in the region between the Hpa I and the Hind III sites, the plasmid being referred to as pWT131 and the phasing from the trp promoter to the Hind III site being changed 2 bp from the plasmid of claim 5; and the nic⁻ derivatives thereof.

8. A process for the production of plasmid pEH3 which comprises digesting a wild-type strain of E./coli with restriction endonuclese Hind III to produce a Hind III/trp E fragment, ligating the fragment to a linear molecule obtained by the restriction of plasmid pBR322 with restriction endonuclease Hind III to produce a combinant plasmid, transforming trpoE$_\Delta$1 E. coli with the combinant plasmid and selecting those E.coli colonies showing tetracycline resistance and tryptophan complementation to obtain the plasmid pEH3.

9. A process for the production of plasmid pEH4 which comprises digesting a wild-type strain of *E. coli* with restriction endonuclease Hind III to produce a Hind III/trp E fragment, litigating the fragment to a linear molecule obtained by the restriction of the plasmid pBR322 with restriction endonuclease Hind III to produce a combinant plasmid, transforming trpoE$_\Delta$1 *E. coli* with the combinant plasmid and selecting those *E. coli* colonies showing tetracycline sensitivity and tryptophan complementation to obtain the plasmid pEH4.

10. A process for the production of plasmid pEH5 which comprises restricting plasmid pEH3 with restriction endonuclease Eco RI to produce a linear molecule, digesting the linear molecule with exonuclease III and S1 nuclease, treating the digested linear molecule with DNA polymerase I, ligating the digested, treated linear molecule with DNA ligase to produce a combinant plasmid, transforming trpoE$_\Delta$1 *E. coli* with the combinant plasmid and selecting for those colonies showing tryptophan complementation and ampicillin resistance to obtain the plasmid pEH5.

11. A process for the production of plasmid pWT101 which comprises restricting plasmid pEH5 with restriction endonuclease Hinf I to obtain a fragment containing the complete tryptophan promoter and cloning the fragment into the Hind III site of the plasmid pBR322 which comprises treating the Hinf I ends of the fragment with DNA polymerase I, ligating the treated fragment with Hind III linkers in the presence of DNA ligase to produce a ligated molecule, treating the ligated molecule with Hind III restriction endonuclease to produce a linear molecule having Hind III sticky ends, ligating the linear molecule into the Hind III site of the plasmid pBR322 to produce a combinant plasmid, transforming *E. coli* K12 HB 101 with the combinant plasmid and selecting those *E. coli* colonies showing ampicillin resistance to obtain the plasmid pWT101.

12. A process for the production of pWT111 which comprises restricting pWT101 with restriction endonuclease Eco RI to produce a linear molecule, digesting the linear molecule with exonuclease III and S1 nuclease, treating the digested linear molecule with DNA polymerase I, religating the treated, digested linear molecule to produce a combinant plasmid, transforming *E. coli* K12 HB101 with the combinant plasmid and selecting those *E. coli* colonies showing ampicillin resistance to obtain the plasmid pWT111.

13. A process for the production of plasmid pWT121 which comprises restricting plasmid pWT111 with restriction endonuclease Hind III to produce a linear molecule, treating the linear molecule with DNA polymerase I, ligating the treated linear molecule with Hind III linker DNA, restricting the ligated molecule with restriction endonuclease Hind III to produce a second linear molecule, religating the second linear molecule, to produce a combinant plasmid, transforming *E. coli* K12 HB101 with the combinant plasmid and selecting those *E. coli* colonies showing ampicillin resistance to obtain the plasmid pWT21.

14. A process for the production of plasmid pWT131 which comprises restricting plasmid pWT121 with restriction endonuclease Hind III to produce linear molecule, treating the linear molecule with DNA polymerase I, ligating the treated linear molecule with Hind III linker DNA, restricting the ligated molecule with restriction endonuclease Hind III to produce a second linear molecule, religating the second linear molecule to produce a combinant plasmid, transforming *E. coli* K12 HB101 with the combinant plasmid and selecting those *E. coli* colonies showing ampicillin resistance to obtain the plasmid pWT131.

* * * * *